United States Patent [19]
Glenn et al.

[11] Patent Number: 6,069,112
[45] Date of Patent: May 30, 2000

[54] METHOD FOR PREVENTING PHYSIOLOGICAL DISORDERS WITHOUT DIMINISHING PHOTOSYNTHESIS

[75] Inventors: David Michael Glenn, Shepherdstown, W. Va.; Dennis G. Sekutowski, Stockton, N.J.; Gary J. Puterka, Shepherdstown, W. Va.

[73] Assignee: Englehard Corporation, Iselin, N.J.

[21] Appl. No.: 09/204,643

[22] Filed: Dec. 2, 1998

Related U.S. Application Data

[63] Continuation-in-part of application No. 08/972,659, Nov. 18, 1997, which is a continuation-in-part of application No. 08/812,301, Mar. 5, 1997, Pat. No. 5,908,708.

[51] Int. Cl.$^7$ .......................... A01N 59/00; A01N 59/06; A01N 59/02

[52] U.S. Cl. .......................... 504/119; 120/126; 120/127; 120/187; 120/188; 71/DIG. 1

[58] Field of Search .................... 504/119, 120, 504/126, 127, 187, 188; 71/DIG. 1

[56] References Cited

U.S. PATENT DOCUMENTS

| | | | |
|---|---|---|---|
| 2,441,423 | 5/1948 | Elliot et al. | 260/29 |
| 2,733,160 | 1/1956 | Ller | 117/16 |
| 2,818,340 | 12/1957 | Goddin et al. | 99/2 |
| 3,120,445 | 2/1964 | Aluisi et al. | 106/286 |
| 3,124,505 | 3/1964 | Doyle et al. | 424/127 |
| 3,159,536 | 12/1964 | Marotta | 167/12 |
| 3,227,657 | 1/1966 | Haden et al. | 252/317 |
| 3,235,451 | 2/1966 | Odeneal | 167/42 |
| 3,346,507 | 10/1967 | Taulli | 252/316 |
| 3,964,649 | 6/1976 | Alexander | 222/399 |
| 4,071,374 | 1/1978 | Minton | 106/189 |
| 4,098,600 | 7/1978 | Chupp | 71/105 |
| 4,203,864 | 5/1980 | Sawyer et al. | 252/314 |
| 4,274,883 | 6/1981 | Lumbeck et al. | 106/308 |
| 4,279,895 | 7/1981 | Carle | 424/127 |
| 4,382,868 | 5/1983 | House | 252/28 |
| 4,632,936 | 12/1986 | Boase et al. | 514/465 |
| 4,634,463 | 1/1987 | Ohsuga | 71/52 |
| 4,705,816 | 11/1987 | Pole | 43/52 |
| 5,122,518 | 6/1992 | Vrba | 514/63 |
| 5,186,935 | 2/1993 | Tucker | 424/410 |
| 5,392,559 | 2/1995 | Long | 43/52 |
| 5,393,461 | 2/1995 | Fillipova | 252/314 |
| 5,414,954 | 5/1995 | Long | 43/121 |
| 5,455,220 | 10/1995 | Dedolph | 504/241 |
| 5,480,638 | 1/1987 | Erwin | 424/614 |
| 5,628,144 | 5/1997 | Eastin | 47/58 |
| 5,656,571 | 8/1997 | Miller et al. | 504/116 |

FOREIGN PATENT DOCUMENTS

| | | | |
|---|---|---|---|
| 53127134 | 11/1978 | Japan | A01G 13/02 |
| 17 92 25 7A | 6/1990 | Russian Federation . | |

OTHER PUBLICATIONS

Section Ch, week 8403, Derwent Publications Ltd., London, GB, Class A97, AN 84–014859, XP002069730 "Hydrophobic Silicic Acid Produce React Alkali Metal Silicate Mineral Acid Treat Product Silicone Oil" Nippon Silica Kogyo KK.

D.M. Glenn, et al. "Hydrophobic Particles For Pest Control in Deciduous Tree Fruit Production" XP002069729. Hortscience, vol. 32, No. 3, 1997, p. 467.

Section CH, week 7421, Derwent Publications Ltd., London, GB, Class A82, AN 74–38844V, XP002069731 "Water Repellent Coatings Based on Silica Fine Powder Paper Wood Concrete Mortar Gypsum Substrate", S. Shimoda.

Driggers, B.F. "Experiments with Talc and Other Dusts Used Against Recently Hatch Larvae of the Oriental and Codling Moths," J. Econ, Ent., 22 327–334 (1929).

Hunt, C.R., "Toxicity of Insecticide Dust Diluents and Carriers to Larvae of the Mexican Bean Beetle," J. Econ. Ent., 40 215–219 (1947).

P. Alexander, J.A. Kitchener and H.V.A. Briscoe, "Inert Dust Insecticides," Parts I, II, and III, Ann. Appl. Biol., 31 143–159 (1944).

W. Ebeling, R. F. Wagner "Rapid Desiccation of Drywood Termites with Inert Sorptive Dusts and Other Substances," J. Econ. Ent., 52 190–207 (1959).

M. Bar–Joseph, H. Frenkel "Spraying Citrus Plants with Kaolin Suspensions Reduces Colonization by The Spiraea Aphid," Crop Port 2 371–374 (1983).

J.S. Dhaliwal, "Effect of Rainfall and Kaolinite Spray on the Corn Aphid, *Rhopalosiphum Maidis* (Fitch) Infesting Barley (Hordeum Vulgare Linn), " Forage Res. 5:155–157 (1979).

A. Boyce, "Mortality of *Ragoletis Completa Cress. (Diptera:Trypetidae)* Through Ingestion of Certain Solid Materials," J. Econ. Ent., 25 1053–1059 (1932).

C. Richardson L. Glover, "Some Effects of Certain 'Inert' and Toxic Substances Upon the Twelve–Spotted Cucumber Beetle, *Diabrotica Duodecimpunctata*, " J. Econ. Ent., 25 1176–1181 (1932).

A. Farmer, "The Effects of Dust on Vegetation: A Review," Envir Pol 79 (1193) 63–75.

V. Wigglesworth, "Action of Inert Dusts on Insects," Nature 153 (1944) 493–494.

W. David, B. Gardiner, "Factors Influencing the Action of Dust Insecticides," Bul Ent. Res. (1950) 41 1–61.

H. Kalmus, "Action of Inert Dusts on Insects," Nature 33 (1945) 188–189.

J. Kring, "Flight Behavior of Aphids," Ann Rev Ent. 17 461–493 (1972).

(List continued on next page.)

*Primary Examiner*—S. Mark Clardy
*Assistant Examiner*—Alton Pryor
*Attorney, Agent, or Firm*—Raymond F. Keller

[57] ABSTRACT

In one embodiment, the present invention relates to a method for preventing sunburn, and other physiological disorders such as watercore, corking and bitterpit, without diminishing photosynthesis, comprising applying to at least a portion of a surface of a plant an effective amount of a finely divided particulate material to prevent sunburn, and other physiological disorders such as watercore, corking and bitterpit, in the plant, wherein the particulate material comprises a heat treated particulate material and the particulate material as applied permits an exchange of gases on the surface of the plant and the particulate material has a thickness from about 1 $\mu$m to about 1,000 $\mu$m.

54 Claims, No Drawings

OTHER PUBLICATIONS

S. Chiu, Toxicity Studies of So–Called 'Inert' Materials with the Bean Weevil, *Acanthoscelides Obtectus* (Say) J. Econ. Ent. 32 240–248 (1939).

M. Baradas, B. Blad, N. Rosenberg, "Reflectant Induced Modification of Soybean Canopy Radiation Balance v. Longwave Radiation Balance," Agron J. 68 329–332 (1976).

G. Stanhill, S. Moreshet, M. Fuchs, "Effect of Increasing Foliage and Soil Reflectivity on the Yield and Water use Efficiency of Grain Sorghum," Agron J. 68 329–332 (1976).

S. Moreshet, S. Cohen, Y. Fuchs, "Effect of Increasing Foliage Reflectance on Yield, Growth and Physiological Behavior of a Dryland Cotton Crop," Crop Sci 19 863–868 (1979).

R. Yokomi, "A Preliminary Report of Reduced Infection by *Spiroplasma Citri* and Virescence in Whitewash–Treated Periwinkle," Phytopathology 71 914 (1981).

D. Eveling, "Similar Effects of Suspensions of Copper Oxychloride and Kaolin on Sprayed Leaves," Ann Apply Biol. (1972) 70, 245–249.

J. Jack, J. Gilbert, "The Effect pf Suspended Clay on Ciliate Population Growth Rates," Freshwater Biol. (1993) 29, 385–394.

H. Uppal, S. Cheema, "Effect of Mulches and Kaolin Spray on Soil Temperature, Growth, Yield and Water Use of Barley," Ind J. Agric Sci (1981) 51, 653–659.

D. Meador, "Reducing Russet on 'Golden Delicious' Apples with Silicon Dioxide Formulation Foliage Sprays," Hort Sci (1977) 12, 504–505.

T. Babu, S. Hussaini, B. Satyanarayana, "Effect of Pre–Storage Seed Treatements on Adult Mortality, Oviposition and Development of *Callosobruchus Chinensis L. (Bruchidae-:Coleoptera* and the Viability of Mungbean *(Vigana Radiata* (L.) Wilczek) in India," Tropical Pest Mgt (1989) 35, 397–398.

T. Babu, S. Hussaini, M. Sriramulu, M. Siddiqui, Effect of Inert Clay and Insect Growth Regulators on the Development of *Callosobruchus Chinesis* L and the Germination of Mungbean Seed [Vigna Radiata(1) Wilczek].

R. Campbell, J. Ephgrave, "Effect of Bentonite Clay on the Growth of *Gaeumannomyces Graminis var. tritici* and on its Interactions with Antagonistic Bacteria," J Gen Microbiol (1983) 129, 771–777.

J. Desmarchelier, C. Ahern, "Insecticide–Rententive Carriers 2. Fernitrothion–Impregnated Clays," Aus J Exper Agric (1988) 28, 271–8.

R. Wagner, W. Ebeling, "Lethality of Inert Dust Materials to Kalotermes Minor Hagen and Their Role as Preventivesin Structural Pest Control," J. Econ. Ent., (1959) 52, 208–212.

J. S. Kennedy, C.O. Booth, W.J.S. Kershaw, "Host Finding by Aphids In the Field," Ann Appl. Biol (1961), 49, 1–21.

W.O. Cline, R.D. Millholland, "Root Dip Treatments for Controlling Blueberry Stem Blight Caused by *Botryosphaeria Dothidea* in Container–Grown Nursery Plants," Plant Disease 76, 136–138 (1992).

J. Norman, "Development of *Colletotrichum Gloesporioides f. sp. Clidemiae* and *Septoria passiflorae* into Two Mycroherbicides with Extended Viability," Plant Disease 79, 1029–1032 (1995).

S. K. Bhattacharyya, M. K. Basu, "Kaolin Powder as a Fungal Carrier," Appl. Envir. Microbio. 44, 751–753 (1982).

R. H. Daines, R. J. Lukens, E. Brennan, I. Leone, "Phytotoxity of Captan as Influenced by Formulation, Environment and Plant Factors," Phytopathology (1957) 47, 567–572.

FDF Yougn, JRM Thacker, DJ Curtis, "The Effects of Three Adjuvants On the Retention of Insecticide Formulations by Cabbage Leaves," J. Environ. Sci. Health (1996) B31, 165–178.

G. Haukenes, BK Hjeltns, "Kinetics of the Binding of Immunoglubulins, Antibodies and Virus Haemagglutination Inhibitors to Kaolin, " Biologicals (1991) 19, 31–35.

J. Han, "Use of Antitranspirant Epidermal Coatings for Plant Protection in China," Plant Dis. (1990) 74, 263–266.

O. Ziv, RA Frederiksen, "The Effect of Film–Forming Anti–Transpirants on Leaf Rust and Powdery Mildew Incidence on Wheat," Plant Path (1987) 36, 242–245.

C. Jacob, et al. "New Strategies in the Control of Major Leaf Disease of Hevea," J. Myco & Plant Path (1195) 25, 120.

S. Marco, "Incidence of Nonpersistently Transmitted Viruses in Pepper Sprayed with Whitewash, Oil, and Insecticide, Alone or Combined," (1993) Plant Dis 77, 1119–1122.

Ziv, O. "Control of Septoria Leaf Blotch of Wheat and Powdery Mildew of Barley with Antitranspirant Epidermal Coating Materials," Phytopar (1983) 11, 33–38.

M. Kamp, "Control of *Erysiphe Cichoracearum* on Zinnia Elegans, with a Polymer–Based Antitranspirant," Hort Sci (1985) 20, 879–881.

J. Zekaria–Oren, Z Eyal, "Effect of Film–Forming Compounds on the Development of Leaf Rust on Wheat Seedlings," Plant Dis (1991) 75, 231–234.

A. Franck, M. Bar–Joseph, "Use of Netting and Whitewash Spray to Protect Papaya Plants Against Nivun Haamir (NH) Dieback Disease," Crop Prot (1992) 11, 525–528.

O. Ziv, "Effects of Bicarbonates and Film–Forming Polymers on Cucurbits Foliar Diseases," Plant Dis (1992) 76, 513–517.

TC Helvey, "Insecticidal effect of Inert Solid Diluents," Sci (1952) 116, 631–632.

HG Guy, HF Dietz "Further Investigations with Japanese Beetle Repellents," J.Econ. Ent., (1939) 32, 248–252.

C. Conceicao, A. Mexia, A. Barbosa, "Combined Effects of Silica Aerogels and Insect Growth Regulators Against *Sitophilus Zeamais* Motch Infestations," Int Cong Ent pro 1996.

MRGK Nair, "Structure of Waterproofing Epicuticular Layers in Insects in Relation to Inert Dust Action," Indian J. Ent. (1957) 19, 37–49.

BR Bartlett, "The Action of Certain 'Inert 'Dust Materials on Parasitic Hymenoptera," J. Econ. Ent. (1951) 44, 891–896.

GL Hockenyos, "The Effect of Dusts on the Oriental Roach," J. Econ. Ent. (1933) 26, 792–794.

T. Hirano, M. Kiyota, I. Aiga, "Physical Effects of Dust on Leaf Physiology of Cucumber and Kidney Bean Plants," Envirn Poll (1995) 89, 255–261.

NKS Rao, "The Effects of Antitranspirants on Leaf Water Status, Stomatal Resistance and Yield in Tomato," J Hort Sci (1985) 60, 89–92.

DW Eveling MZ Eisa, "The Effects of a Cuticle—Damaging Kaolin On Herbicidal Phytoxicity," Weed Res (1976) 16, 15–18.

S. Marco, O. Ziv, R. Cohen, "Suppression of Powdery Mildew in Squash by Applications of Whitewash, Clay and Antitranspirant Materials," Phytopar (1194) 22, 19–29.

SM Lipson, G. Stotzky, "Effect of Kaolinite on the Specific Infectivity of Reovirus," FEMS Micr. Let. 37, 83–88 (1986).

S. Lavie, G. Storzky, "Adhesion of the Clay Minerals Montmorillonite, Kaolinite, and Attapulgite reduces Respiration of *Histoplasma Capsulatum*," App & Envir Micro (1986) 51, 65–73.

MS Rajan, KR Reddy, RS Rao, GHS Reddi, "Effect of Antitranspirants and Reflectants on Pod Yield of Rainfed Groundnut, " Agri Sci Dig (1981) 1, 205–206.
W. Ebeling, RJ Pence, "Termites and Other Enemies of Wood," Pest Cont. Oct. 1956, 46–64.
DW Eveling, A. Bataille, "The Effect of Deposits of Small Particles on the Resistance of Leaves and Petals to Water Loss," Envirn Poll (1984) 36, 229–238.
M. Llewellyn, J. Ervaz, "Abrasive Dusts as a Mechanism for Aphid Control," Ent. Exp. & Appl. 26 (1979) 219–222.
M. Swamiappan, S. Jayaraj, KC Chandy, "Effect of Activated Kaolinitic Clay on Some Storage Insects," Z. Ang. Ent. 80 (1976), 385–389.
D Permual, G Le Paturel, Laboratory Evaulation of Acid–Activated Kaolin to Protect Stored Paddy Against Infestation by Stored Product Insects, J. Stored Prod. Res. 26, 149–153, 1990.
D Permual, G Le Patourel, "Small Bin Trials to Determine the Effectiveness of Acid—Activated Kaolin Against Four Species of Beetles Infesting Paddy Under Tropical Storage Conditions," J. Stored Prod. Res. 28, 193–199 (1992).
DT Lowery, MK Sears, CS Harmer, "Control of Turnip Mosaic Virus of Rutabaga With Applications of Oil, Whitewash, and Insecticides," J. Econ. Ent. (1990) 83, 2352–2356.
S. Marco, "Incidence of Aphid—Transmitted Virus Infections Reduced by Whitewash Sprays on Plants," Amer, Phytop (1986) 76, 1344–1348.
J. Basnizki, M. Evenari, "The Influence of a Reflectant on Leaf Temperature and Development of the Globe Artichoke (*Cynara scolymus L.*)," J. Am Soc Hort Sci 100, 109–112 (1975).
EF Durner, TJ Gianfagna, "Interactions of Ethephon, Whitewashing, and Dormant Oil on Peach Pistil Growth, Hardiness and Yield," Am Hort Sci 27, 104–105 (1992).
EF Durner, TJ Gianfagna "Peach Pistil Growth Inhibition and Subsequent Bloom Delay by Midwinter Bud Whitewashing," Am Hort Sci 25, 1222–1224 (1990).
WJ Lipton, "Temperatures and Net Heat Gain in Normal and Whitewashed Cantaloupe Fruits," J. Amer. Hort. Sci. 97, 242–244 (1972).
WJ Lipton, F. Matoba, "Whitewashing to Prevent Sunburn of 'Crenshaw 'Melons," Hortscience, 6, 343–345 (1971).
WS Cranshaw DJ Liewehr, "Effects of Colored Sprays on Aphid & Psyllid Colonization," SW Entomol 15, 205–209 (1990).
S. Marco, "Possible Modes of Action of Whitewash in Reducing Virus Incidence in Potatoes," Potato Res 33, 138–139 (1990).
I. Bar–Zakay, M. Gokkes, Y. Oren, "Chemical Control of Aphids on Citrus Bearing Trees," Phytoparasitica 15, 343 (1987).
S. Marco, "Reducing the Incidence of Aphid—Transmitted Viruses by Reflective Materials," Phytoparasitica 13, 279–280 (1985).
DJ Gumpf, GN Oldfield, RK Yokomi, "Progress in the Control of Citrus Stubborn Disease," Proc Int. Soc. Citric, 457–458 (1981).
JGM Vos, TS Uhan, B. Sutarya, "Intergrated Crop Management of Hot Peppers," Crop Prot. 14, 445–452 (1995).
CG Summers, JJ Stapleton, AS Duncan, DA Hart, "Comparison of Sprayable and Film Mulches in Delaying the Onset of Aphid—Transmitted Virus Diseases in Zucchini Squash," Plant Dis (1995) 79, 1126–1131.
PC Nicot, M. Mermier, BE Vaissiere, J. Lagier, "Differential Spore Production for *Botrytis Cinerea* on Agar Medium and Plant Tissue Under Near—Ultraviolet Light—Absorbing Polyethylene Film," Plant Dis (1196) 80, 555–558.
JJ Stapleton, WK Asai, JE De Vay, "Use of Polymer Mulches in Intergrated Pest Management Programs for Establishment of Perennial Fruit Crops," (1989) Acta Hort. 255, 161–168.
RE Byers, CG Lyons, "Effect of Chemical Deposits from Spraying Adjacent Rows on Efficacy of Peach Bloom Thinners," HortSci (1985) 20, 1076–1078.
RE Byers, KS Yoder, GE Mattus, "Reduction in Russetting of 'Golden Delicious Apple' with 2, 4, 5–TP and Other Compounds," HortScience 18:63–65 (1983).
RE Byers, DH Carbaugh, CN Presley, "'Stayman ' Fruit Cracking as Affected by Surfactants, Plant Growth Regulators, and Other Chemicals," J. Amer. Soc. Hort. Sci. 155:405–411 (1990).

METHOD FOR PREVENTING PHYSIOLOGICAL DISORDERS WITHOUT DIMINISHING PHOTOSYNTHESIS

CROSS-REFERENCE TO RELATED APPLICATIONS

This application is a continuation-in-part of U.S. patent application Ser. No. 08/972,659, filed Nov. 18, 1997, which is a continuation-in-part of U.S. patent application Ser. No. 08/812,301, filed Mar. 5, 1997, now U.S. Pat. No. 5,908,708 both of which are incorporated herein by reference for their teachings related to the invention disclosed herein.

FIELD OF THE INVENTION

The present invention is directed to methods for protecting plants from extreme environmental conditions and preventing physiological disorders including sunburn without diminishing photosynthesis.

BACKGROUND OF THE INVENTION

Food production on land areas experiences extreme environmental conditions in the above-ground environment. Environmental conditions include variation in air temperature, wind speed, light levels, relative humidity and available nutrients and water. Methods for protecting plants from extreme environmental conditions are desired since they would increase the amount and stability of food production.

While foliage reflectance is recognized as a means of moderating environmental extremes, such techniques result in reduced photosynthesis. Generally speaking, foliage sprays cause a long-term reduction in the rate of $CO_2$ uptake (photosynthesis) and enhance leaf senescence. Thus, although plant survival may increase with a foliar application of a reflective material, decreased transpiration and decreased photosynthesis undesirably occurs. Photosynthesis and transpiration in plants are positively linked in that a decrease in transpiration generally leads to a decrease in photosynthesis.

For example, reflective coatings are applied to the surfaces of fruits and vegetables to reduce excessive heat and light (including ultraviolet (UV) light and infrared (IR) light) at the fruit surface in an attempt to prevent a condition known as "sunburn". While the precise cause of sunburn is unknown, sunburn is a disorder that appears as a darkened area on the surface of fruits and vegetables. Beneath the sunburned area, the fruit tissue is damaged and likely to develop disease symptoms. The combination of off-color and increased disease susceptibility makes the fruit unmarketable. The strategy of applying a reflectant treatment is to reduce the temperature of the fruit by reflecting heat or by blocking light including UV and IR light.

Reducing fruit temperature by spraying the fruit with water, evaporative cooling, reduces other apple physiological disorders such as watercore, corking and bitterpit. Evaporative cooling is also used to reduce sunburn. The application of evaporative cooling water increases yield by increasing available water to the plant and increasing photosynthesis. However, the negative aspects of high costs, high maintenance, and the possibility of being subjected to water restrictions are associated with evaporative cooling.

In perennial crop production such as tree fruit, flower buds for the subsequent year are initiated while fruit are developing for the current growing season. In practice, a plant may or may not produce flower buds for the subsequent year. One of the many biochemical cues to develop flower buds is the rate of photosynthesis and the availability of photosynthetically derived carbohydrates for flower bud development.

The availability of carbohydrates is limited by the photosynthetic capacity of the plant and the pool of carbohydrates is partitioned between the competing carbohydrate needs of the woody tissue, leaf tissue, developing flower buds and developing fruit. If photosynthesis is limited by excessive heat or water stress during the flower bud initiation period, flower bud initiation is reduced and fewer flowers are produced the following season. Reduced flower number results in reduced fruit number. In the subsequent year, the tree has a reduced number of fruit and it develops excessive numbers of flower buds because it lacks the competing developing fruit when flower buds are initiated. The alternating production of large and small numbers of fruit is an undesirable condition known as "alternate bearing".

A related problem to alternate bearing is called "excessive fruit drop". Normal fruit drop occurs when, simultaneously, the fruit is developing, tree growth is occurring, and flower buds are being initiated. Photosynthetically derived carbohydrates become limiting to all the growing tissues at this time in the growing season and the plant aborts the developing fruit, and limits the initiation of flower buds. When environmental conditions deleteriously effects or diminishes photosynthesis, fruit drop is excessive. Furthermore, UV and IR radiation may have damaging effects on plant tissue. UV and/or excessive IR radiation damage the photosynthetic mechanism of plants and reduce plant productivity.

Various materials are used to 1) reduce winter damage; 2) delay the onset of bloom in order to avoid spring frosts; and 3) prevent UV radiation damage. However, there are problems associated with applying various materials to fruits. For example, while various materials may address one or more of the three above mentioned concerns, these materials tend to diminish photosynthesis. Another problem relates to the difficulty of providing inert and low toxicity materials for use with plants. Yet another problem is easily and/or thoroughly cleaning or rinsing materials from fruits.

SUMMARY OF THE INVENTION

The present invention provides methods of reducing sunburn, and other physiological disorders such as watercore, corking and bitterpit, by reducing excessive heat and light at the plant surface without diminishing photosynthesis. The present invention provides methods of reducing heat and water stress thereby reducing the potential for alternate bearing to develop. The present invention also provides methods of limiting environmental extremes that reduce photosynthesis and thereby increase the availability of carbohydrates, thus reducing fruit drop.

The present invention provides methods of increasing the solute content of plant cells thereby increasing the cell resistance to freeze dehydration. In other words, increasing cell solute content reduces the potential for freezing events to dehydrate cells below a point where cell death occurs. The present invention also provides methods that reduce UV radiation at the plant surface and reduce this environmental stress and increase photosynthesis.

This invention relates to a method for enhancing the photosynthesis of plants such as horticultural crops which comprises applying to the surface of a plant an effective amount of one or more highly reflective particulate materials, the particulate materials being finely divided, and wherein the particles as applied allow for the exchange of gases on the surface of the plant.

In one embodiment, the present invention relates to a method for preventing sunburn, and other physiological disorders such as watercore, corking and bitterpit, without diminishing photosynthesis of the plant, comprising applying to at least a portion of a surface of a plant an effective amount of a finely divided particulate material to prevent sunburn, and other physiological disorders such as watercore, corking and bitterpit, in the plant, wherein the particulate material comprises a heat treated particulate material heated to a temperature from about 300° C. to about 1,200° C. and the particulate material as applied permits an exchange of gases on the surface of the plant and the particulate material film has a thickness from about 1 μm to about 1,000 μm.

In yet another embodiment, the present invention relates to a method of reducing fruit drop, comprising applying to at least a portion of a surface of a plant an effective amount of a finely divided particulate material to increase availability of carbohydrates in the plant, the particulate material comprising at least 25% by weight of a calcined kaolin wherein the particulate material as applied permits an exchange of gases on the surface of the fruit plant and the particulate material forms a continuous particulate material film over the portion of the plant surface to which it is applied, and a maximum average size of openings in the continuous particulate material film is less than about 100 μm.

In yet another embodiment, the present invention relates to a method of increasing plant cell resistance to freeze dehydration, comprising applying to at least a portion of a surface of a plant comprising plant cells an effective amount of a finely divided particulate material to increase the solute content of plant cells in the plant, the particulate material comprising at least 25% by weight of a calcined kaolin wherein the particulate material as applied permits an exchange of gases on the surface of the plant and the particulate material forms a continuous particulate material film over the portion of the fruit plant surface to which it is applied covering from about 75% to about 100% of the surface.

DETAILED DESCRIPTION OF THE INVENTION

This invention relates to methods for enhancing the photosynthesis of plants, such as methods for protecting plants from extreme environmental conditions without diminishing photosynthesis. In one embodiment, the present invention relates to applying particulate materials, which may form a protective film, on a plant thereby reducing the effects of extreme environmental conditions on the plant while enhancing horticultural effects. In another embodiment, the present invention relates to protecting plants from extreme environmental conditions in which the surface of a plant is coated with a film comprising one or more layers of a particulate material, the particulate materials being finely divided. The effects of extreme environmental conditions on the plant are reduced or eliminated while photosynthesis is not diminished.

Photosynthesis is a process by which photosynthetic plants utilize solar energy to build carbohydrates and other organic molecules from carbon dioxide and water. The conversion of carbon dioxide to such organic molecules is generally referred to as carbon fixation or photosynthesis and, in most plants, occurs by the reductive pentose phosphate cycle, generally referred to as the C-3 cycle. An additional biochemical pathway of carbon fixation is generally referred to as the C-4 pathway. The effects of enhanced photosynthesis are typically observed by increased yields/productivity, e.g., increased fruit size or production (usually measured in weight/acre), improved color, increased soluble solids, e.g. sugar, acidity, etc., and reduced plant temperature.

The plants to which the present invention relates include horticultural crops such as actively growing agricultural crops, fruiting agricultural crops, actively growing ornamental crops, fruiting ornamental crops and the products thereof. Specific examples include fruits, vegetables, trees, flowers, grasses, and landscape plants and ornamental plants. Particularly preferred plants include apple trees, pear treas, peach trees, plum trees, lemon trees, grapefruit trees, avocado trees, orange trees, apricot trees, walnut trees, tomato plants, cauliflower plants, grape vines, and pepper plants.

In one embodiment, the particulate materials suitable for use in the present invention are highly reflective. As used herein, "highly reflective" means a material having a "Block Brightness" of at least about 80 and preferably at least about 90 and more preferably at least about 95 as measured by TAPPI standard T 452. Measurements can be made on a Reflectance Meter Technidyne S-4 Brightness Tester manufactured by Technidyne Corporation which is calibrated at intervals not greater than 60 days using brightness standards (paper tabs and opal glass standards) supplied by the Institute of Paper Science or Technidyne Corporation. Typically a particle block or plaque is prepared from 12 grams of a dry (<1% free moisture) powder. The sample is loosely placed in a cylinder holder and a plunger is slowly lowered over the sample to a pressure of 29.5–30.5 psi and held for about 5 seconds. The pressure is released and the plaque is examined for defects. A total of three plaques are prepared and three brightness values are recorded on each plaque by rotating the plaque about 120 degrees between readings. The nine values are than averaged and reported.

The particulate materials suitable for use in the present invention are heat treated particulate materials. For purposes of this invention, heat treated particulate materials are particulate materials that have been heated to an elevated temperature and include baked particulate materials, calcined particulate materials, and fired particulate materials. Heat treated particulate materials are hydrophilic. Specific examples include calcined calcium carbonate, calcined talc, calcined kaolin, baked kaolin, fired kaolin, calcined bentonites, calcined clays, calcined pyrophyllite, calcined silica, calcined feldspar, calcined sand, calcined quartz, calcined chalk, calcined limestone, calcined precipitated calcium carbonate, baked calcium carbonate, calcined diatomaceous earth, calcined barytes, calcined aluminum trihydrate, calcined pyrogenic silica, and calcined titanium dioxide.

Heat treatment in accordance with the invention involves heating a particulate material at a temperature from about 300° C. to about 1,200° C. for about 10 seconds to about 24 hours. In a preferred embodiment, heat treatment involves heating a particulate material at a temperature from about 400° C. to about 1,100° C. for about 1 minute to about 15 hours. In a more preferred embodiment, heat treatment involves heating a particulate material at a temperature from about 500° C. to about 1,000° C. for about 10 minutes to about 10 hours. The heat treatment may be carried out in air, in an inert atmosphere or under a vacuum.

In most embodiments, the particulate materials contain at least about 25% by weight, and particularly about 25% to about 100% by weight of heat treated particulate materials. In another embodiment, the particulate materials contain at least about 40% by weight, and particularly about 40% to about 99% by weight of heat treated particulate materials. In yet another embodiment, the particulate materials contain at least about 60% by weight, and particularly about 60% to about 95% by weight of heat treated particulate materials. In still yet another embodiment, the particulate materials contain at least about 70% by weight, and particularly about 70% to about 90% by weight of heat treated particulate materials.

In one embodiment, the heat treated particulate material comprises a heat treated kaolin, such as a calcined kaolin. In another embodiment, the heat treated particulate material comprises a hydrophobic treated heat treated kaolin. Examples of preferred heat treated particulate materials that are commercially available from Engelhard Corporation, Iselin, N.J. are the calcined kaolins sold under the trademark Satintone® and the siloxane treated calcined kaolins sold under the trademark Translink®.

In addition to the heat treated particulate materials, the particulate materials may optionally further include supplemental particulate materials such as hydrophilic or hydrophobic materials and the hydrophobic materials may be hydrophobic in and of themselves, e.g., mineral talc, or may be hydrophilic materials that are rendered hydrophobic by application of an outer coating of a suitable hydrophobic wetting agent (e.g., the particulate material has a hydrophilic core and a hydrophobic outer surface).

In one embodiment, the particulate materials contain about 1% to about 75% by weight of supplemental particulate materials. In another embodiment, the particulate materials contain about 5% to about 60% by weight of supplemental particulate materials. In yet another embodiment, the particulate materials contain about 10% to about 30% by weight of supplemental particulate materials.

Typical supplemental particulate hydrophilic materials suitable for use in the present invention include: minerals, such as calcium carbonate, talc, hydrous kaolins, bentonites, clays, pyrophyllite, silica, feldspar, sand, quartz, chalk, limestone, precipitated calcium carbonate, diatomaceous earth and barytes; functional fillers such as aluminum trihydrate, pyrogenic silica, and titanium dioxide.

The surfaces of hydrophobic supplemental or heat treated materials can be made hydrophobic by contact with hydrophobic wetting agents. Many industrial mineral applications, especially in organic systems such as plastic composites, films, organic coatings or rubbers, are dependent upon just such surface treatments to render the mineral surface hydrophobic; see, for example, Jesse Edenbaum, *Plastics Additives and Modifiers Handbook,* Van Nostrand Reinhold, New York, 1992, pages 497–500 which is incorporated herein by reference for teachings of such surface treatment materials and their application. So-called coupling agents such as fatty acids and silanes are commonly used to surface treat solid particles as fillers or additives targeted to these industries. Such hydrophobic agents are well known in the art and common examples include: organic titanates such as Tilcom® obtained from Tioxide Chemicals; organic zirconate or aluminate coupling agents obtained from Kenrich Petrochemical, Inc.; organofunctional silanes such as Silquest® products obtained from Witco or Prosil® products obtained from PCR; modified silicone fluids such as the DM-Fluids obtained from Shin Etsu; and fatty acids such as Hystrene® or Industrene® products obtained from Witco Corporation or Emersol® products obtained from Henkel Corporation (stearic acid and stearate salts are particularly effective fatty acids and salts thereof for rendering a particle surface hydrophobic).

Examples of preferred supplemental particulate materials that are commercially available include calcium carbonate commercially available from English China Clay under the trademarks Atomite® and Supermite® and stearic acid treated ground calcium carbonates commercially available from English China Clay under the trademarks Supercoat® and Kotamite®.

In one embodiment, the particulate materials do not include calcium hydroxide. In other words, in one embodiment, the plant treatment does involve applying calcium hydroxide with or without other particulate materials to a plant.

The term "finely divided" when utilized herein means that the particulate materials have a median individual particle size below about 10 microns and preferably below about 3 microns and more preferably the median particle size is about one micron or less. Particle size and particle size distribution as used herein are measured with a Micromeritics Sedigraph 5100 Particle Size Analyzer. Measurements were recorded in deionized water for hydrophilic particles. Dispersions were prepared by weighing 4 grams of dry sample into a plastic beaker adding dispersant and diluting to the 80 ml mark with deionized water. The slurries were then stirred and set in an ultrasonic bath for 290 seconds. Typically, for kaolin 0.5% tetrasodium pyrophosphate is used as a dispersant; with calcium carbonate 1.0% Calgon T is used. Typical densities for the various powders are programmed into the sedigraph, e.g., 2.58 g/ml for kaolin. The sample cells are filled with the sample slurries and the X-rays are recorded and converted to particle size distribution curves by the Stokes equation. The median particle size is determined at the 50% level.

In one embodiment, the particulate material has a particle size distribution wherein up to 90% by weight of the particles have a particle size of under about 10 microns. In another embodiment, the particulate material has a particle size distribution wherein up to 90% by weight of the particles have a particle size of below about 3 microns. In a preferred embodiment, the particulate material has a particle size distribution wherein up to 90% by weight of the particles have a particle size of about one micron or less. In this connection, the particulate material according to the present invention has a relatively narrow particle size distribution.

The particulate materials particularly suitable for use in this invention are inert and have low toxicity. As used herein "inert" particulate materials are particles that are not phytotoxic. The particulate materials preferably have extremely low toxicity meaning that in the quantities needed for effective enhanced horticultural effects, the particulate materials are not considered harmful to animals, the environment, the applicator and the ultimate consumer.

As previously discussed, this invention relates to horticultural crops wherein the surface of said crop is treated with one or more particulate materials. This treatment should not materially affect the exchange of gases on the surface of said crop. The gases which pass through the particle treatment are those which are typically exchanged through the surface skin of living plants. Such gases typically include water vapor, carbon dioxide, oxygen, nitrogen and volatile organics.

The surface of a plant, such as a horticultural crop, is treated with an amount of one or more highly reflective, finely divided particulate materials that is effective in protecting plants from extreme environmental conditions without diminishing photosynthesis of the plant. The extent of treatment coverage of a plant can be determined by one skilled in the art. Full coverage is preferred. Full coverage of areas in direct sunlight is also preferred. Less than full plant coverage is within the scope of this invention and can be highly effective, for example, neither the under surface of the plant (that which is not exposed directly to the source of light) need be treated by the method of this invention nor must the upper surface of the plant be completely covered; although full or substantially full plant substrate coverage is preferred. Particularly, full or substantially full fruit (or area where protection is desired) coverage is preferred, as other areas of a plant do not require such treatment. Full or substantially full plant substrate coverage can provide additional benefits such as effective disease control, smoother fruit surface, reduced bark and fruit cracking, and reduced russeting. Reference is made to U.S. Ser. No. 08/972,648, filed on Nov. 11, 1997, entitled "Treated Horticultural Substrates" which is incorporated herein by reference for its teachings regarding methods for achieving these additional benefits. The method of the present invention may result in a residue of the treatment forming a membrane of one or more layers of highly reflective particulate materials on the plant surface.

The particulate materials suitable for use in the present invention may be applied as a slurry of finely divided particles in a volatile liquid such as water, a low boiling organic solvent or low boiling organic solvent/water mixture. Adjuvants such as surfactants, dispersants, speaders/stickers (adhesives), wetting agents, antifoaming agents, and/or drift reducing agents may be incorporated in preparing an aqueous slurry of the particulate materials of this invention.

In one embodiment, the slurry of finely divided particles consists essentially of the particulate materials and water and optionally at least one of supplemental particulate materials, low boiling organic solvents, surfactants, dispersants, speaders/stickers, wetting agents, antifoaming agents, and drift reducing agents.

Surfactants and dispersants include nonionic surfactants, anionic surfactants, cationic surfactants and/or amphoteric surfactants and promote the ability of the particulate materials to remain in solution during spraying (contribute to a better quality slurry). Surfactants and dispersants also function to break-up agglomerates of particulate materials.

Speaders/stickers promote the ability of the particulate materials to adhere to plant surfaces. Wetting agents reduce surface tension of water in the slurry and thus increase the surface area over which a given amount of the slurry may be applied. Antifoaming agents decreases foaming during spraying. Drift reducing agents prevent droplets from becoming too small thus reducing the ability of slurry droplets to drift during spraying.

One or more layers of the slurry can be sprayed or otherwise applied to the plant surface. The volatile liquid is preferably allowed to evaporate between coatings. The residue of this treatment may be hydrophilic or hydrophobic. Applying particles as a dust or brushing, although not being commercially practical on a large scale due to drift, inhalation hazards and poor residuality, is an alternative for carrying out the method of this invention. Spraying is a preferred method of application.

Spreader/stickers that can be mixed with hydrophilic particles (3% or more solids in water) to aid in spraying uniform treatments on a plant or horticultural substrate are: modified phthalic glycerol alkyd resins such as Latron B-1956 from Rohm & Haas Co.; plant oil based materials (cocodithalymide) with emulsifiers such as Sea-wet from Salsbury lab, Inc.; polymeric terpenes such as Pinene II from Drexel Chem. Co.; nonionic detergents (ethoxylated tall oil fatty acids) such as Toximul 859 and Ninex MT-600 series from Steppan. In one embodiment, the spreader/stickers do not include latex type materials.

In another embodiment, the amount of adjuvants in the aqueous slurry of the particulate materials is from about 0.01% by weight to about 20% by weight. In yet another embodiment, the amount of adjuvants in the aqueous slurry of the particulate materials is from about 0.1% by weight to about 10% by weight. In still yet another embodiment, the amount of adjuvants in the aqueous slurry of the particulate materials is from about 0.5% by weight to about 5% by weight.

The particle treatment may be applied as one or more layers of finely divided particulate material. The amount of material applied is within the skill of one of ordinary skill in the art. The amount will be sufficent to protect plants from extreme environmental conditions without diminishing photosynthesis of the plant to which these particles are applied. Typically, this treatment is most effective when plant surface is white in appearance. For example, this can be accomplished by applying from about 25 up to about 5000 micrograms of particulate material/$cm^2$ of plant surface for particles having specific density of around 2–3 $g/cm^3$, more typically from about 100 up to about 3000 micrograms of particulate material/$cm^2$ of plant surface for particles having specific density of around 2–3 $g/cm^3$, and preferably from about 100 up to about 500 micrograms of particulate material/$cm^2$ of plant surface for particles having specific density of around 2–3 $g/cm^3$. As the brightness of the highly reflective particles increases lesser amounts of these brighter particles are necessary to be effective for the purposes of this invention. In addition, environmental conditions such as wind and rain may reduce plant coverage of the highly reflective particulate materials and therefore it is within the scope of this invention to apply the highly reflective particles one or more times during the growing season of said horticultural plant so as to maintain the desired effect of invention.

In embodiments where the inventive treatment prevents sunburn, and other physiological disorders such as watercore, corking and bitterpit, without diminishing photosynthesis, the particulate materials are preferably applied to portions of a plant that receive direct sunlight. This may be accomplished by applying the particulate materials to the entire plant or to the sun-ward surfaces of the plant. Alternatively, this may be accomplished by applying the particulate materials to the entire fruit or to the sun-ward surfaces of the fruit.

The low boiling organic liquids useful in the present invention are preferably water-miscible and contain from 1 to about 6 carbon atoms. The term "low boiling" as used herein shall mean organic liquids which have a boiling point generally no more than about 100° C. These liquids contribute to the ability of the particulate materials to remain in finely divided form without significant agglomeration. Such low boiling organic liquids are exemplified by: alcohols such as methanol, ethanol, propanol, i-propanol, i-butanol, and the like, ketones such as acetone, methyl ethyl ketone and the like, and cyclic ethers such as ethylene oxide, propylene oxide and tetrahydrofuran. Combinations of the above-mentioned liquids can also be employed. Methanol is the preferred low boiling organic liquid.

Low boiling organic liquids may be employed in applying the particles to plant substrates for the purposes of this invention. Typically, the liquids are used in an amount sufficient to form a dispersion of the particulate material. The amount of low boiling organic liquid is typically up to about 30 volume percent of the dispersion, preferably from about 3 up to about 5 volume percent, and most preferably from about 3.5 to about 4.5 volume percent. The particulate material is preferably added to a low boiling organic liquid to form a slurry and then this slurry is diluted with water to form an aqueous dispersion. The resulting slurry retains the particles in finely divided form wherein most of the particles are dispersed to a particle size of less than about 10 microns.

After the slurry is applied to a plant, the slurry is permitted to dry (the volatile liquids evaporate) wherein a continuous or substantially continuous film of the particulate materials is formed. By continuous, it is meant that, where applied, the dry film is continuous (or substantially continuous). For example, in an embodiment where the upper third of a fruit is covered with particulate material in accordance with the present invention, the film covering the upper third of the fruit is continuous or substantially continuous while the bottom two-thirds of the fruit is not covered with the particulate material.

Of the covered portion of a plant surface, the particulate material film is continuous in that it covers from about 75% to about 100% of the surface area, thus the openings or noncontinuous areas the particulate material film constitutes from about 0% to about 25% of the surface area. In another embodiment, the particulate material film is continuous in that it covers from about 90% to about 99.9% of the surface area, thus the openings or noncontinuous areas the particulate material film constitutes from about 0.1% to about 10% of the surface area. In yet another embodiment, the particulate material film is continuous in that it covers from about 95% to about 99% of the surface area, thus the openings or noncontinuous areas the particulate material film constitutes from about 5% to about 1% of the surface area.

In the continuous particulate material film, the maximum average size (average diameter) of pores or noncontinuous areas in the film is generally less than about 100 $\mu$m. In another embodiment, the maximum average size of openings or noncontinuous areas in the particulate material film is generally less than about 10 $\mu$m. In yet another embodiment, the maximum average size of openings or noncontinuous areas in the particulate material film is generally less than about 5 $\mu$m.

The thickness of the particulate material film applied using a slurry ranges from about 1 $\mu$m to about 1,000 $\mu$m. In another embodiment, the thickness of the particulate material film ranges from about 3 $\mu$m to about 750 $\mu$m. In yet another embodiment, the thickness of the particulate material film ranges from about 5 $\mu$m to about 500 $\mu$m.

Although continuous, the particulate material film permits the exchange of gases (water and carbon dioxide transpiration and photosynthesis, respectively) on the portions of the surface of a plant to which it is applied. In this connection, the continuous particulate material film is gas permeable or porous, but not discontinuous.

The particulate material film formed in accordance with the present invention effectively blocks (absorbs, scatters and/or reflects away) excessive UV and/or IR radiation that has damaging effects on plant tissue. In one embodiment, the particulate material film formed in accordance with the present invention blocks (absorbs, scatters and/or reflects away) from about 1% to about 10% of the UV and/or IR radiation to which it is exposed. In another embodiment, the particulate material film formed in accordance with the present invention blocks from about 2% to about 5% of the UV and/or IR radiation to which it is exposed. As a result, the photosynthetic and biochemical mechanisms of plants are not substantially damaged by UV and/or IR radiation. The present invention in this embodiment provides a method that reduces UV and/or IR radiation at the plant surface that in turn reduces the environmental stress and increases photosynthesis.

The particulate material film formed in accordance with the present invention reduces the heat load on the plant and prevents the breaking of dormancy during the late winter due to increased plant temperature.

The particulate material film formed in accordance with the present invention prevents cold damage by increasing the carbohydrate content of the plant tissues as a defense to water freezing in the plant. This is because when a plant freezes, the plant cells initially supercool below 0° C., after which extracellular water freezes and ice propagates throughout the extracellular spaces. As the ice propagates, intracellular water moves out of the cell and freezes extracellularly. Water continues to move out of the cell as freezing continues and this process concentrates the solutes of the cell and dehydrates the cell. Severe dehydration will kill cells, tissues, and the whole plant. The solute content of the plant cell controls how much water is lost, for a high solute content reduces dehydration. Thus, the particulate material film, by in some embodiments increasing photosynthesis increases cell solute content and reduces the potential for freezing events to dehydrate cells below a point where cell death occurs. In one embodiment, the present invention involves a method that reduces environmental stress that increases photosynthesis and the solute content of plant cells thus increasing the cell resistance to freeze dehydration.

The particulate material film formed in accordance with the present invention can be readily and easily removed from plants which are so treated. In one embodiment, the particulate material film can be and easily removed from plants or fruits using a high pressure water sprayer, wherein the water contains or does not contain a suitable surfactant. The identity of the surfactant depends upon the specific identity of the particulate material, whether or not any adjuvants are present, and the amount of any adjuvant, if any. In another embodiment, the particulate material film can be and easily removed from plants or fruits using a water bath or water spray, wherein the water contains or does not contain a suitable surfactant, and optionally brushing the plant or fruit.

Although the particulate materials are applied over plants, the particulate materials do not diminish the photosynthesis of the plants. In other words, contrary to conventional treatments that prevent physiological disorders while undesirably diminishing photosynthesis, the present invention provides particulate materials that are applied over plants to prevent one or more physiological disorders while not diminishing photosynthesis. In one embodiment, application of the particulate materials in accordance with the present invention enhance the photosynthesis of the treated plants.

The following examples are illustrative of embodiments of the invention and are not intended to limit the invention as encompassed by the claims forming part of the application.

EXAMPLE 1

"Red Delicious" apple trees received the following treatments: 1) Conventional pesticide applications applied according to the presence of economic levels of pests using the Virginia, West Virginia and Maryland Cooperative Extension 1997 Spray Bulletin for Commercial tree Fruit Growers publication 456–419, 2) no treatment, 3) weekly application of Translink® 77 beginning in Mar. 11, 1997, 4) weekly application of calcined kaolin (Satintone® 5HP) beginning in Apr. 29,1997, and 5) weekly application of treated calcium carbonate (SuperCoat® commercially available from English China Clay) beginning in Apr. 29, 1997. Treatments (3) and (5) applied 25 pounds material suspended in 4 gal methanol and added to 100 gal water. Treatment (4) applied 25 pounds material suspended in 100 gal water with the addition of 27 oz Ninex® MT-603 and 2 pints Toximul. These treatments were applied at the rate of 125 gal/acre using an orchard sprayer. This mixture was applied at the rate of 125 gal/acre using an orchard sprayer. The treatments were arranged in a randomized complete block design with 4 replications and 3 trees/plot. Treatments were not irrigated and received 21.58 cm of precipitation from May 1 to Aug. 30, 1997. Fruit were harvested at maturity; fruit number, weight and color were measured. Color was measured using a Hunter colorimeter. Color values represent Hunter "a" value units, in which increasing value represents increasing red color. Photosynthesis and stomatal conductance were measured on Aug. 6 and 8, 1997. Photosynthesis and stomatal conductance data were collected using a Licor 6300 photosynthesis system. Increasing values of photosynthesis and stomatal conductance represent increasing assimilation of carbon dioxide from the atmosphere and transpiration of water from the leaf, respectively; both parameters reflect improved plant productivity when values increase. Treatments (1) and (3) were measured twice daily at 10 to 11 am and 2 to 3 pm. Three trees in each plot were measured with 2 sunlit leaves/tree. Canopy temperature was measured using an Everest Interscience (Model 110) infrared thermometer with +/−0.5° C. accuracy, in which the temperature of the plant surface approximately 1 m in diameter was determined on the sunlit side of the tree. Data for canopy temperature are presented as the difference between leaf and air temperature. A negative canopy temperature denotes a canopy cooler than air temperature due to transpiration and heat reflection. The data are reported in Table I.

TABLE I

| Treatment | Yield/tree (kg) | Fruit weight (g) | Red Color | Photosynthesis rate ($\mu$moles $CO_2$/ $m^2$/sec) | Stomatal conductance (mol/ $m^2$/ sec) | Canopy- (Air) Temperature (C.) |
| --- | --- | --- | --- | --- | --- | --- |
| Conventional | 43.7 | 136 | 19.7 | 6.7 | 0.35 | −4.2 |
| Control | 30.1 | 123 | 23.2 | | | |
| Translink ® 77 | 51.6 | 135 | 23.9 | 9.2 | 0.57 | −5.2 |
| Calcined Kaolin | 37.6 | 124 | 21.0 | | | |
| Treated $CaCO_3$ | 39.1 | 130 | 24.1 | | | −5.5 |

The use of hydrophobic kaolin (Translink® 77) increased yield compared to conventional management (51.6 vs 43.7 kg, respectively) without a meaningful reduction in fruit size (135 vs 136 g/fruit).

The use of hydrophobic kaolin (Translink® 77) improved fruit color compared to the conventional management (23.9 vs 19.7). Treated $CaCO_3$ (SuperCoat®) and calcined Kaolin (Satintone® 5HB) also improved color compared to the conventional management (24.1 and 21.0 vs 19.7). The untreated control improved color compared to the conventional management (23.2 vs 19.7) but this is likely due to defoliation of the tree due to poor pest control since no pesticides were applied (see Lord and Greene, Ibid.). Defoliation from pest damage increases light to the fruit surface which increases color development. Pest control levels were adequate in all other treatments and did not result in defoliation.

Average precipitation approximates 35.6 cm from April 1 to August 30; precipitation was 40% below normal.

The application of Translink® 77 increased photosynthesis, stomatal conductance and reduced plant temperature. Stomatal conductance is a measure of the width of stomates on the underside of the leaf. Water loss, in the form of transpiration, occurs through the stomates and is controlled by the size of the stomatal opening. The greater the size of the opening, the greater is the stomatal conductance, and so transpiration is greater. Similarly, the greater the size of the stomatal opening, the greater is the influx of carbon dioxide necessary for photosynthesis. Canopy temperature was reduced by the application of Translink® 77 due to the increased transpirational cooling of the leaf related to increased stomatal conductance resulting from the application of Translink® 77 and the IR reflectance. The application of calcium carbonate (SuperCoat®) also reduced plant temperature, presumably due to increased transpirational cooling of the leaf related to increased stomatal conductance and the IR reflectance.

Yakima,

"Red Delicious" apple trees received the following treatments: 1) no treatment; this untreated control did not have pest pressures that exceeded the threshold for pesticide application, 2) application of Translink® 77 on April 5, May 8, 29; June 25; July 14; September 4, 3) application of Translink® 77 on the same dates as "(2)" and on May 22, June 9, and July 31. Treatments (2) and (3) applied 25 pounds material suspended in 4 gal methanol and added to 96 gal water. This mixture was applied at the rate of 100 gal/acre using an orchard sprayer. The treatments were arranged in a randomized complete block design with 3 replications of 3 trees/plot. Treatments were all irrigated on a weekly basis to meet plant water needs using sprinkler irrigation located beneath the trees. Photosynthesis and stomatal conductance were measured on Jul. 17 to 20, 1997. Photosynthesis data were collected using a Licor 6300 photosynthesis system. Treatments (1), (2) and (3) were measured twice daily at 10 to 11 am and 2 to 3 pm. Three trees in each plot were measured with 2 sunlight leaves/tree. Data are the mean values for all days and hours sampled. Canopy temperature was measured using an Everest Interscience Infrared (Model 110) thermometer with +/−0.5° C. accuracy, in which the temperature of the plant surface approximately 1 meter in diameter was determined on the sunlit side of the tree. Data for canopy temperature are presented as the difference between leaf and air temperature. A negative canopy temperature denotes a canopy cooler than air temperature due to transpiration and heat reflection. Canopy temperature data were collected from Aug. 17 to 20, 1997. The data presented in Table II are representative of the entire data set. At the time of harvest, 20 fruit were randomly collected from each of the 3 trees/plot (total of 180 fruit/treatment). Fruit were weighed and color determined. Color was determined with a Hunter calorimeter. Color values represent Hunter "a" values. These data are not presented in Table II

TABLE II

| Treatment | Fruit weight (g/fruit) | Photosynthesis ($\mu$mol $CO_2/m^2$/sec) | Stomatal conductance (mol/$m^2$/sec) | Canopy- (air) temperature (°C.) |
|---|---|---|---|---|
| Control | 164 | 8.8 | 0.24 | −4.5 |
| Translink ® 77 applied 7 times | 177 | 11.8 | 0.43 | −5.7 |
| Translink ® 77 applied 10 times | 195 | 12.9 | 0.46 | −6.0 |

Fruit size increased with increasing applications of Translink® 77.

Trees in the study had fruit size greater than the study in Kearneysville, W.Va. due to the use of irrigation. The reduced canopy temperature of both Translink® 77 treatments illustrates that the application of these particles can reduce plant temperature.

The application of Translink® 77 increased photosynthesis, stomatal conductance and reduced plant temperature. Canopy temperature was reduced by the application of Translink® 77 due to the increased transpirational cooling of the leaf related to increased stomatal conductance resulting from the application of Translink® 77 and the IR reflectance. Reducing the frequency of application from 7 applications did reduce photosynthesis, stomatal conductance, and canopy temperature compared to 10 applications, demonstrating that there is a beneficial response to increasing amounts of Translink® 77 coverage.

EXAMPLE 3

Santiago, Chile

"September Lady" peach, spaced 4 m×6 m, received the following treatments: 1) Conventional pesticide application applied according to the presence of economic levels of pests, 2) no treatment, 3) weekly application of Translink® 77 beginning Oct. 29, 1996. Treatment (3) applied 25 pounds material suspended in 4 gal methanol and added to 96 gal water. This mixture was applied at the rate of 100 gal/acre using a high pressure hand sprayer. Treatments were irrigated weekly using surface irrigation. Fruit were harvested at maturity and the number and weight measured. The data are reported in Table III.

TABLE III

| Treatment | Yield/tree (kg) | Fruit weight (g) | Fruit number/tree |
|---|---|---|---|
| Conventional | 13.9 | 156 | 94 |
| Control | 14.6 | 139 | 109 |
| Translink ® 77 | 25.4 | 137 | 156 |

The use of hydrophobic kaolin (Translink® 77) increased yield compared to the conventional treatment and the control by increasing the number of fruit/tree. Fruit size was reduced, although not statistically, from 156 to 137 g due to the larger number of fruit on the peach tree (94 vs 156).

EXAMPLE 4

Biglerville, Pa.—Dan Pack Orchard

"Golden Delicious" apples received 3 treatments: 1) commercial pesticide application applied according to the presence of economic levels of pests using the Virginia, West Virginia and Maryland Cooperative Extension 1997 Spray Bulletin for Commercial tree Fruit Growers publication 456–419, 2) full rate of Translink® 77, and 3) half rate of Translink® 77. Treatments (2) and (3) applied 25 and 12.5 pounds material, respectively, suspended in 4 and 2 gal methanol, respectively, and added to 100 gal water. This mixture was applied at the rate of 200 gal/acre using an orchard sprayer. The treated area was approximately 1 acre plots with 2 replications of each treatment in a randomized block design. At harvest the plots were commercially harvested and processed by a commercial grading line. At the time of grading, 100 fruit from each plot were randomly chosen to determine fruit size, color, and surface defects. Color was determined using a Hunter calorimeter. Green color values represent Hunter "a" values in which higher values represent less green color, a beneficial trait in "Golden Delicious" apple. The data are reported in Table IV.

TABLE IV

| Treatment | Fruit size (mm) | Green color |
|---|---|---|
| Translink ® 77 full rate | 69 | −8.0 |
| Translink ® 77 half rate | 67 | −8.9 |
| Conventional | 67 | −10.0 |

Application of Translink® 77 at the full and half rate reduced green color, and Translink® 77 at the full rate increased fruit size compared to the half rate and conventional treatment.

"Stayman" apples received 2 treatments: 1) commercial pesticide application applied according to the presence of economic levels of pests using the Virginia, West Virginia and Maryland Cooperative Extension 1997 Spray Bulletin for Commercial tree Fruit Growers publication 456–419, 2) Translink® 77 treatment applied 25 pounds material suspended in 4 gal methanol and added to 96 gal water. This mixture was applied at the rate of 200 gal/acre using an orchard sprayer. Each treatment was applied to 1 acre blocks with no randomization. Apples were harvested commercially and processed on a commercial grading line. Data presented represent percent packout from the commercial grading line. The data are reported in Table V.

TABLE V

| Treatment | Fruit size (mm) | <2.5 inches (%) | 2.5–2.75 inches (%) | 2.75–3.0 inches (%) | >3.0 inches (%) |
|---|---|---|---|---|---|
| Translink ® 77 | 69 | 11 | 38 | 44 | 7 |
| Conventional | 62 | 66 | 28 | 6 | 0 |

The application of Translink® 77 increased the packout of larger fruit and reduced the losses due to small fruit (<2.5 inches) compared to the conventional treatment.

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

What is claimed is:

1. A method for reducing at least one of sunburn, watercore, corking, and bitterpit, without diminishing photosynthesis, comprising:

applying to at least a portion of a surface of a plant an effective amount of a finely divided particulate material to form a particulate material film and reduce at least one of sunburn, watercore, corking, and bitterpit, in the plant, the finely divided particulate materials have a median individual particle size below about 3 microns, wherein the particulate material comprises a heat treated particulate material heated to a temperature from about 300° C. to about 1,200° C. and the particulate material as applied permits an exchange of gases on the surface of plant and the particulate material film has a thickness from about 1 μm to about 1,000 μm.

2. The method according to claim 1 wherein the particulate material is applied to at least the portion of the surface of the plant by spraying.

3. The method of claim 1 wherein the heat treated particulate materials are hydrophobic.

4. The method of claim 1 wherein the heat treated particulate materials do not comprise calcium hydroxide.

5. The method of claim 1 wherein the particulate material has a particle size distribution wherein most of the particles have a particle size of under about 10 microns.

6. The method of claim 1 wherein the particulate material comprises a hydrophilic core and a hydrophobic outer surface.

7. The method of claim 6 wherein the particulate material further comprises one or more of calcium carbonate, mica, hydrous kaolin, bentonite, clays, pyrophyllite, silica, feldspar, sand, quartz, chalk, limestone, diatomaceous earth, baryte, aluminum trihydrate, and titanium dioxide.

8. The method of claim 1 wherein the heat treated particulate materials comprise one or more of calcined calcium carbonate, calcined talc, calcined kaolin, calcined bentonites, calcined clays, calcined pyrophyllite, calcined silica, calcined feldspar, calcined sand, calcined quartz, calcined chalk, calcined limestone, calcined precipitated calcium carbonate, calcined diatomaceous earth, calcined barytes, calcined aluminum trihydrate, calcined pyrogenic silica, and calcined titanium dioxide.

9. The method of claim 6 wherein said hydrophobic outer surface materials are selected from the group consisting of organic titanates, organic zirconate or aluminate coupling agents, organofunctional silanes, modified silicone fluids and fatty acids and salts thereof.

10. The method of claim 1 wherein the plant is selected from actively growing or fruiting agricultural and ornamental crops.

11. The method of claim 1 wherein the plant is selected from the group consisting of fruits, vegetables, trees, flowers, grasses, roots, seeds and landscape and ornamental plants.

12. The method of claim 1 wherein the particulate materials comprise about 25% to about 100% by weight of heat treated particulate materials.

13. The method of claim 1 wherein the particulate materials comprise about 40% to about 99% by weight of heat treated particulate materials.

14. A method of reducing at least one of fruit drop and biennial bearing, comprising:
applying to at least a portion of a surface of a fruit plant an effective amount of a finely divided particulate material to form a particulate material film and increase availability of carbohydrates in the fruit plant, the particulate material comprising at least about 25% by weight of a calcined kaolin, the particulate material has a particle size distribution wherein most of the particles have a particle size of under about 10 microns,
wherein the particulate material as applied permits an exchange of gases on the surface of the fruit plant and the particulate material forms a continuous particulate material film over the portion of the fruit plant surface to which it is applied, and a maximum average size of openings in the continuous particulate material film is less than about 100 μm.

15. The method of claim 14 wherein the finely divided particulate material has a median individual particle size below about 3 microns.

16. The method of claim 15 wherein the finely divided particulate materials are applied one or more times during the growing season of said horticultural crop.

17. A method of increasing plant cell resistance to freeze dehydration, comprising:
applying to at least a portion of a surface of a plant comprising plant cells an effective amount of a finely divided particulate material to increase the solute content of plant cells in the plant, the particulate material comprising at least about 25% by weight of a calcined kaolin,
wherein the particulate material as applied permits an exchange of gases on the surface of the plant and the particulate material forms a continuous particulate material film over the portion of the fruit plant surface to which it is applied covering from about 75% to about 100% of the surface.

18. The method of claim 17 wherein the plant is selected from the group consisting of fruits, vegetables, trees, flowers, grasses, roots, seeds and landscape and ornamental plants.

19. The method of claim 17 wherein the particulate materials further comprise at least one of calcium carbonate, talc, hydrous kaolin, bentonites, clays, pyrophyllite, silica, feldspar, sand, quartz, chalk, limestone, precipitated calcium carbonate, diatomaceous earth, barytes, aluminum trihydrate, pyrogenic silica, and titanium dioxide.

20. The method of claim 17 wherein the particulate materials are applied by spraying in a slurry form.

21. A method for reducing at least one of sunburn, watercore, corking, and bitterpit, without diminishing photosynthesis, comprising:
applying to at least a portion of a surface of a plant an effective amount of a slurry to reduce at least one of sunburn, watercore, corking, and bitterpit, in the plant,
wherein the slurry consists essentially of a heat treated particulate material and water and optionally at least one of supplemental particulate materials, low boiling organic solvents, surfactants, dispersants, speaders/stickers, wetting agents, antifoaming agents, and drift reducing agents, the slurry as applied permits an exchange of gases on the surface of plant and the applied slurry has a thickness from about 1 μm to about 1,000 μm wherein most of the heat treated particulate materials have a particle size of less than about 10 microns.

22. A method for reducing at least one of sunburn, watercore, corking, and bitterpit, without diminishing photosynthesis, comprising:
applying to at least a portion of a surface of a plant an effective amount of a finely divided particulate material to form a particulate material film and reduce at least one of sunburn, watercore, corking, and bitterpit, in the plant, the particulate material comprises a hydrophilic core and a hydrophobic outer surface,
wherein the particulate material comprises a heat treated particulate material heated to a temperature from about 300° C. to about 1,200° C. and the particulate material as applied permit s a n exchange of gases on the surface of plant and the particulate material film has a thickness from about 1 μm to about 1,000 μm.

23. The method according to claim 22 wherein the particulate material is applied to at least the portion of the surface of the plant by spraying.

24. The method of claim 22 wherein the heat treated particulate material does not comprise calcium hydroxide.

25. The method of claim 22 wherein the particulate material has a particle size distribution wherein most of the particles have a particle size of under about 10 microns.

26. The method of claim 22 wherein the particulate material further comprises one or more of calcium carbonate, mica, hydrous kaolin, bentonite, clays, pyrophyllite, silica, feldspar, sand, quartz, chalk, limestone, diatomaceous earth, baryte, aluminum trihydrate, and titanium dioxide.

27. The method of claim 22 wherein the heat treated particulate material comprises one or more of calcined calcium carbonate, calcined talc, calcined kaolin, calcined bentonites, calcined clays, calcined pyrophyllite, calcined silica, calcined feldspar, calcined sand, calcined quartz, calcined chalk, calcined limestone, calcined precipitated calcium carbonate, calcined diatomaceous earth, calcined barytes, calcined aluminum trihydrate, calcined pyrogenic silica, and calcined titanium dioxide.

28. The method of claim 22 wherein said hydrophobic outer surface material is selected from the group consisting of organic titanates, organic zirconate or aluminate coupling agents, organofunctional silanes, modified silicone fluids and fatty acids and salts thereof.

29. The method of claim 22 wherein the plant is selected from actively growing or fruiting agricultural and ornamental crops.

30. The method of claim 22 wherein the plant is selected from the group consisting of fruits, vegetables, trees, flowers, grasses, roots, seeds and landscape and ornamental plants.

31. The method of claim 22 wherein the finely divided particulate material has a median individual particle size below about 3 microns.

32. The method of claim 22 wherein the particulate material comprises about 25% to about 100% by weight of heat treated particulate materials.

33. The method of claim 22 wherein the particulate material comprises about 40% to about 99% by weight of heat treated particulate materials.

34. A method for reducing at least one of sunburn, watercore, corking, and bitterpit, without diminishing photosynthesis, comprising:
applying to at least a portion of a surface of a plant an effective amount of a finely divided particulate material to form a particulate material film and reduce at least one of sunburn, watercore, corking, and bitterpit, in the plant, the heat treated particulate materials do not comprise calcium hydroxide, wherein the finely divided particulate materials have a median individual particle size below about 3 microns,
wherein the particulate material comprises a heat treated particulate material heated to a temperature from about 300° C. to about 1,200° C. and the particulate material as applied permits an exchange of gases on the surface of plant and the particulate material film has a thickness from about 1 μm to about 1,000 μm.

35. The method according to claim 34 wherein the particulate material is applied to at least the portion of the surface of the plant by spraying.

36. The method of claim 34 wherein the heat treated particulate material is hydrophobic.

37. The method of claim 34 wherein the particulate material has a particle size distribution wherein most of the particles have a particle size of under about 10 microns.

38. The method of claim 34 wherein the particulate material comprises a hydrophilic core and a hydrophobic outer surface.

39. The method of claim 38 wherein the particulate material further comprises one or more of calcium carbonate, mica, hydrous kaolin, bentonite, clays, pyrophyllite, silica, feldspar, sand, quartz, chalk, limestone, diatomaceous earth, baryte, aluminum trihydrate, and titanium dioxide.

40. The method of claim 34 wherein the heat treated particulate material comprises one or more of calcined calcium carbonate, calcined talc, calcined kaolin, calcined bentonites, calcined clays, calcined pyrophyllite, calcined silica, calcined feldspar, calcined sand, calcined quartz, calcined chalk, calcined limestone, calcined precipitated calcium carbonate, calcined diatomaceous earth, calcined barytes, calcined aluminum trihydrate, calcined pyrogenic silica, and calcined titanium dioxide.

41. The method of claim 38 wherein said hydrophobic outer surface material is selected from the group consisting of organic titanates, organic zirconate or aluminate coupling agents, organofunctional silanes, modified silicone fluids and fatty acids and salts thereof.

42. The method of claim 34 wherein the plant is selected from actively growing or fruiting agricultural and ornamental crops.

43. The method of claim 34 wherein the plant is selected from the group consisting of fruits, vegetables, trees, flowers, grasses, roots, seeds and landscape and ornamental plants.

44. The method of claim 34 wherein the particulate material comprises about 25% to about 100% by weight of heat treated particulate materials.

45. The method of claim 34 wherein the particulate material comprises about 40% to about 99% by weight of heat treated particulate materials.

46. A method for reducing at least one of sunburn, watercore, corking, and bitterpit, without diminishing photosynthesis, comprising:
applying to at least a portion of a surface of a plant an effective amount of a hydrophobic finely divided particulate material to form a particulate material film and reduce at least one of sunburn, watercore, corking, and bitterpit, in the plant,
wherein the hydrophobic particulate material comprises a heat treated particulate material heated to a temperature from about 300° C. to about 1,200° C. and the hydrophobic particulate material as applied permits an exchange of gases on the surface of plant and the particulate material film has a thickness from about 1 μm to about 1,000 μm, wherein most of the heat particulate materials have a particle size of less than about 10 microns.

47. The method according to claim 46 wherein the particulate material is applied to at least the portion of the surface of the plant by spraying.

48. The method of claim 46 wherein the particulate material further comprises one or more of calcium carbonate, mica, hydrous kaolin, bentonite, clays, pyrophyllite, silica, feldspar, sand, quartz, chalk, limestone, diatomaceous earth, baryte, aluminum trihydrate, and titanium dioxide.

49. The method of claim 46 wherein the heat treated particulate material comprises one or more of calcined calcium carbonate, calcined talc, calcined kaolin, calcined bentonites, calcined clays, calcined pyrophyllite, calcined silica, calcined feldspar, calcined sand, calcined quartz, calcined chalk, calcined limestone, calcined precipitated calcium carbonate, calcined diatomaceous earth, calcined barytes, calcined aluminum trihydrate, calcined pyrogenic silica, and calcined titanium dioxide.

50. The method of claim 46 wherein the plant is selected from actively growing or fruiting agricultural and ornamental crops.

51. The method of claim 46 wherein the plant is selected from the group consisting of fruits, vegetables, trees, flowers, grasses, roots, seeds and landscape and ornamental plants.

52. The method of claim 46 wherein the finely divided particulate materials have a median individual particle size below about 3 microns.

53. The method of claim 46 wherein the particulate material comprises about 25% to about 100% by weight of heat treated particulate materials.

54. The method of claim 46 wherein the particulate material comprises about 40% to about 99% by weight of heat treated particulate materials.

* * * * *

UNITED STATES PATENT AND TRADEMARK OFFICE
CERTIFICATE OF CORRECTION

PATENT NO. : 6,069,112
DATED : May 30, 2000
INVENTOR(S) : David Michael Glenn, Dennis G. Sekutowski and Gary J. Puterka It is certified that error appears in the above-identified patent and that said Letters Patent is hereby corrected as shown below:

<u>Title page,</u>
Item [73], the Assignees should read -- Engelhard Corporation, Iselin, New Jerey USA -- and -- The United States of America, as represented by the Secretary of Agriculture, Washington, D.C., USA --.

Signed and Sealed this

Fourteenth Day of May, 2002

*Attest:*

JAMES E. ROGAN
*Attesting Officer*     *Director of the United States Patent and Trademark Office*